US00PP09791P

United States Patent [19]

Rowe

[11] Patent Number: Plant 9,791

[45] Date of Patent: Feb. 4, 1997

[54] PLANTAIN PLANT 'FHIA-21'

[75] Inventor: Phillip R. Rowe, La Lima, Honduras

[73] Assignee: Fundación Hondureña de Investigación Agrícola, San Pedro Sula, Honduras

[21] Appl. No.: 535,552

[22] Filed: Sep. 28, 1995

[51] Int. Cl.[6] ..... A01H 5/00

[52] U.S. Cl. ..... Plt./33.1

[58] Field of Search ..... Plt./33.1

[56] References Cited

U.S. PATENT DOCUMENTS

P.P. 8,983 11/1994 Rowe ..... Plt./33.1

*Primary Examiner*—James R. Feyrer
*Attorney, Agent, or Firm*—Pravel, Hewitt, Kimball & Krieger

[57] ABSTRACT

As compared with the reference False Horn plantain variety, this new and distinct variety of plantain (genus Musa, interspecific hybrid) plant has the following unique combination of desirable features:

1. Leaves are resistant to the black Sigatoka leaf spot disease (*Mycosphaerella fijiensis*) which is a very serious disease on False Horn.
2. Fruits are straighter and the peels have a lighter green color than those of False Horn.
3. Fruit sizes (length and diameter) are similar to those of False Horn when the recommended practice of pruning the bunch to leave only 5 hands for development is followed.
4. Total fingers per bunch and bunch weights at maturity are about double (even when the bunch is pruned to leave 5 hands) those of False Horn.
5. Fried green chips have a very good flavor and are slightly softer than those of False Horn.
6. Ripe fruits have an excellent flavor and texture when microwaved (a higher fruit moisture content and a softer ripe texture make this new variety more suitable than False Horn for this method of cooking).
7. Peels of green fruit turn an attractive uniform yellow color when left to ripen under ambient conditions without ethylene treatment.

3 Drawing Sheets

ORIGIN OF THE VARIETY

This new variety was developed at the Fundación Hondureña de Investigación Agrícola (FHIA) at La Lima, Honduras from a cross made in 1983. It was selected in 1986 from several first generation seedlings from the cross AVP-67×SH-3142 (both unpatented). AVP-67 is the code name for a French plantain which was collected in Honduras and is in FHIA's germplasm collection. (French plantain is the name given to plants with distinctive bunch features which arise as occasional spontaneous mutations in the naturally evolved False Horn variety. As compared to False Horn, the French plantain mutants have about double the number of fruits per bunch, have more slender fruits at maturity, and have a well developed male bud which continues to grow as the fruits mature instead of deteriorating shortly after bunch emergence. Because of consumer preference for fruits with larger diameters, French plantains are not widely grown commercially.) SH-3142, which was developed by inventor, is a bred diploid which is resistant to races 1 and 4 of Panama disease (*Fusarium oxysporum* f. sp. *cubense*), to the burrowing nematode (*Radopholus similis*), and to the black Sigatoka leaf spot disease (*Mycosphaerella fijiensis*). SH-3142 was derived from crossing the SH-1734 bred diploid onto the Pisang Jari Buaya natural diploid which was collected from Papua New Guinea. (The diploids in the FHIA germplasm collection which are in the pedigree of SH-1734 are Lidi, Sinwobogi and a *Musa acuminata* subsp. *errans* wild fully seeded type which were collected as natural clones in Sumatra, Papua New Guinea and the Philippines, respectively.) FHIA-21 was selected as a tetraploid hybrid which maintained the essential plantain-like plant and bunch features of its AVP-67 parental line, but differs from AVP-67 by having a much larger bunch size and a high level of resistance to the black Sigatoka disease. FHIA-21 fruit is also readily distinguished from that of AVP-67 by the color of the peel when green and the texture of the pulp when ripe. The peel color of FHIA-21 is a much lighter green and the ripe pulp is noticeably softer when compared to both AVP-67 and the False Horn reference clone.

ASEXUAL REPRODUCTION OF THE VARIETY

This new plantain plant was asexually reproduced by corms as performed by inventor in the experimental farm of FHIA in La Lima, Honduras and shows that all plant and fruit characteristics run true to the original selected plant and are identical in all respects.

SUMMARY OF THE VARIETY

This new and distinct variety of plantain is a vigorous plant which produces large bunches of fruit. Individual fruits from unpruned bunches differ in size and shape from those of the reference False Horn clone (which is presently the predominant plantain grown worldwide both for domestic consumption and for export) by being slightly shorter and noticeably more slender at maturity. However, if the bunches of the new plant are reduced in size by pruning to leave only the first 5 hands (of the up to 10 total hands which are produced naturally) immediately after bunch emergence, the individual fruit size and shape of these remaining 5 hands are straighter but otherwise very similar to False Horn at maturity. Even when left with only 5 hands, the new plant has about twice the number of fruits and has mature bunch weights about double those of False Horn under the same growing conditions. Fried green chips of FHIA-21 have a very good flavor and are slightly softer than those of False Horn. Ripe fruits have an excellent flavor when microwaved (a higher fruit moisture content and a softer ripe texture make this new variety more suitable than False Horn for this method of cooking). Peels of green fruit of FHIA-21 turn an attractive uniform yellow color when left to ripen under ambient conditions without etylene treatment. This new plant is resistant to the black Sigatoka leaf spot disease which is a very serious disease on the False Horn clone. Thus, FHIA-21 could be grown with considerably less fungicide usage than that required to control this disease on the current False Horn. Interest in this new variety is that it is the first known bred plantain which has disease resistance and fruit quality characteristics which make it a candidate for being cultivated on a large scale.

DESCRIPTION OF THE PHOTOGRAPHS

The accompanying photographic reproductions show typical specimens of the new plantain variety.

Figure 2:
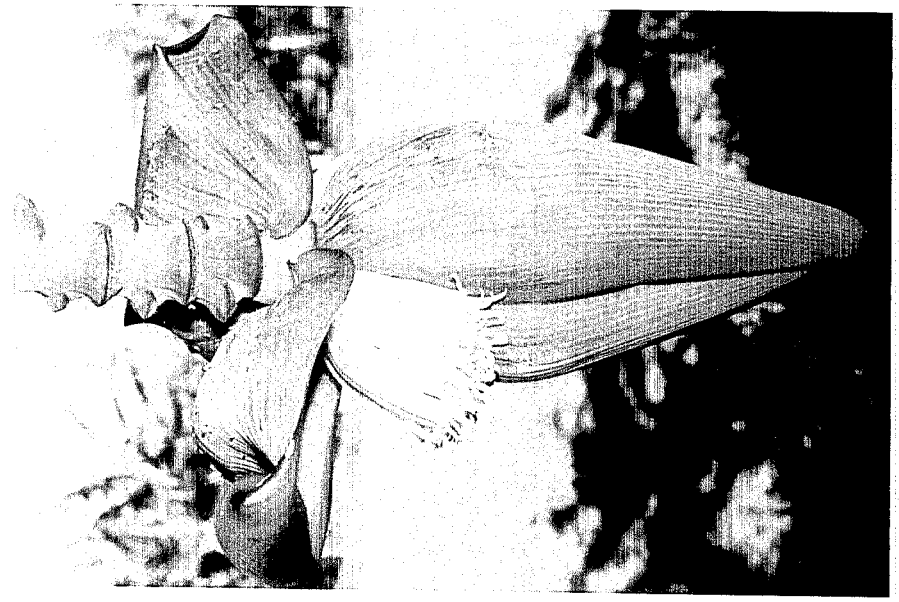
FIG. 2 shows a male bud of a typical FHIA-21 Plantain Plant shortly after the transition from female to male flowers.
Figure 1:
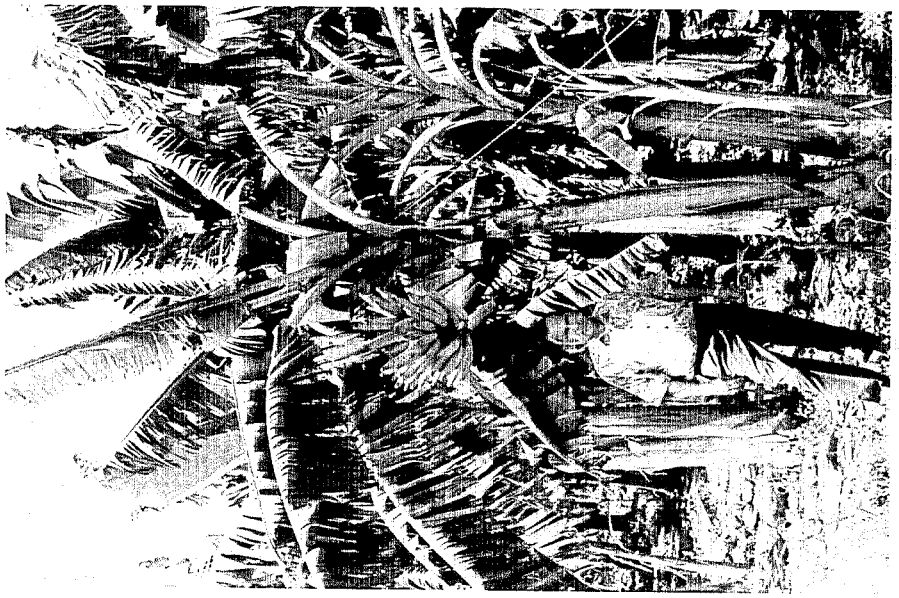
FIG. 1 shows a typical FHIA-21 Plantain Plant with a bunch (which was pruned to leave the first 5 hands at bunch emergence) ready for harvest in the first fruiting cycle.
Figure 4:
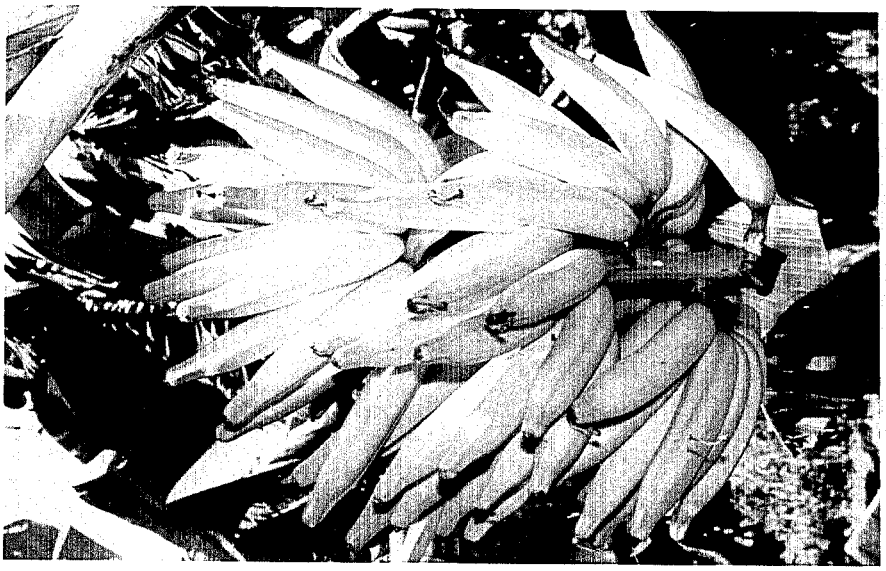
FIG. 4 shows a hanging bunch (which was pruned to leave the first 5 hands at bunch emergence) of the new variety at stage for harvest.
Figure 3:
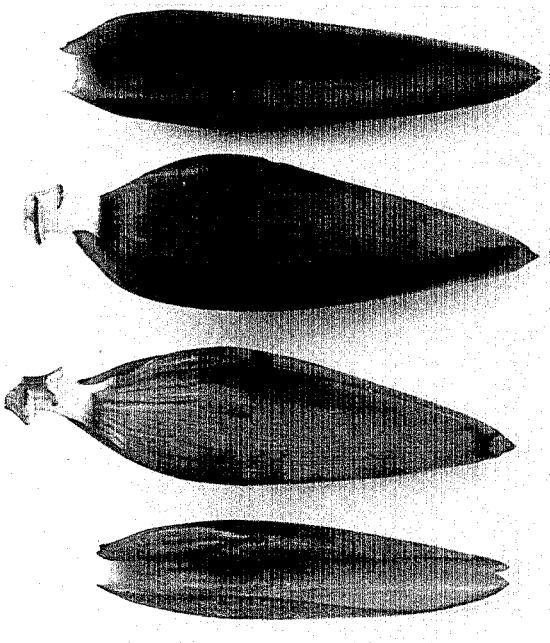
FIG. 3 shows detached newly formed male buds with the outer bract removed before it lifts naturally to depict botanically distinguishing size, shape and color differences in these plant parts of the AVP-67 French plantain variety (left) as compared to FHIA-21. Inside surface color of this outer bract for the new variety conforms to Plate 6-L-8.
Figure 5:
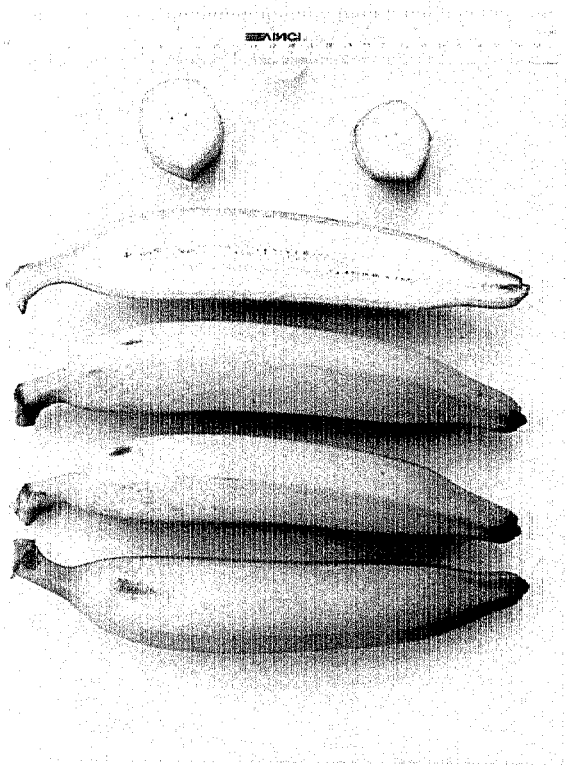
FIG. 5 shows representative whole fingers, a longitudinal section, and cross-sections of fruit at harvest stage of the new variety (marker is 30 cm). These fingers are from a bunch which was pruned in accordance with the recommended practice of leaving only the first 5 hands for development after bunch emergence.

The photographs were taken on fresh material and the colors are as nearly true as is reasonably possible in color representations of this type.

DESCRIPTION OF THE VARIETY

The following is a detailed botanical description of the new and distinct variety of plantain plant, its flowers, foliage and fruit as based on observations of specimens grown in the FHIA experimental farm near La Lima, Honduras. These descriptions are in accordance with the internationally standardized "Descriptor List for Bananas" elaborated by the Institut de Recherches sur les Fruits et Agrumes in Montpellier, France. Color terminology for the peel of green fruit and for the male bud and bracts, which have distinctive colors for variety identification, is in accordance with the Maerz and Paul Dictionary of Color. Other colors are given in common terms for bananas and plantains.

Vegetative characteristics (general growth/pseudostems/suckers):

*Ploidy.*—Tetraploid (AAAB).
*General appearance.*—Normal.
*Characteristics of dwarfism.*—No.
*Size.*—Large.
*Stature.*—Normal.
*Color of pseudostem.*—Light green.
*Appearance of pseudostem.*—Dull.
*Predominant color at the inside base of outer leaf sheath.*—Light green.
*Pigmentation of internal leaf sheaths.*—Pink.
*Color of the sap.*—Watery.
*Wax on leaf sheaths.*—Little.
*Number of suckers* (>30 *cm*).—From 3 to 5.
*Development of suckers.*—No inhibition.
*Position of growth of suckers.*—Vertical growth.

Vegetative characteristics (petioles/midribs/leaves):

*Blotches at the base of the petiole.*—Extensive pigmentation.
*Color of blotches.*—Dark brown.
*Petiole canal of leaf six.*—Margins curved inwards.
*Petiole margins.*—Winged and clasping the pseudostem.
*Type of margin.*—Dry.
*Line of color along edge of petiole margin.*—Yes.
*Color of petiole margin.*—Pink/red.
*Width of petiole margin.*—Wide.
*Length of leaf six.*—Long (220–260 cm).
*Width of leaf six.*—Medium (70–80 cm).
*Length of petiole.*—Medium (50–70 cm).
*Color of upper surface of leaf.*—Green.
*Appearance of upper surface of leaf.*—Dull.
*Color of lower surface of leaf.*—Medium green.
*Appearance of lower surface of leaf.*—Dull.
*Presence of wax on leaves.*—None.
*Insertion of leaf.*—±Symmetric.
*Base of leaf.*—One side rounded.
*Corrugation of leaf.*—Medium corrugation.
*Color of dorsal face of midrib.*—Light green.
*Color of ventral face of midrib.*—Medium green.
*Color of dorsal face of cigar leaf.*—Green.
*Leaves of young suckers.*—With blotches.

Inflorescence (general appearance/male bud):

*Length of peduncle.*—Medium.
*Number of empty nodes on peduncle.*—One.
*Size of peduncle.*—Medium.
*Color of peduncle.*—Medium green.
*Hairiness of peduncle.*—Very hairy, short hairs.
*Position of bunch.*—Slightly angled.
*Shape of bunch.*—Asymmetric.
*Appearance of bunch.*—Lax.
*Flowers forming the fruit.*—Female.
*Fingers of the bunch.*—Biseriate.
*Position of rachis.*—At an angle.
*Appearance of rachis.*—Bare.
*Presence of male bud.*—Present.
*Shape of male bud.*—Intermediate.
*Size of male bud.*—Medium.

Bracts:

*Shape of the base of the bract.*—Medium.
*Shape of apex of bract.*—Intermediate.
*Imbrication of the bract.*—Young bracts slightly overlap.
*Color of the external face of the bract.*—Purple (Plate 56-H-7).
*Color of the internal face of the naturally lifted bract.*—Red/crimson (Plate 47-L-1).
*Color of the apex of the bract.*—Tinted with yellow.
*Stripes of color on bract.*—No.
*Bract scars on rachis.*—Very prominent.
*Fading of color at the base of the inside of the bract.*—Color homogenous.
*Shape of the male bract.*—Width/length greater than 0.30.
*Lifting of male bracts.*—Lifting one or two at a time.

*Behavior of bracts.*—Revolute.
*Presence of wax on the bract.*—Average wax.
*Presence of grooves on the bract.*—Intermediate.

Male flowers:

*Behavior of male flowers.*—Falling before the bract.
*Basic color of compound tepal.*—Cream.
*Pigmentation of compound tepal.*—Absent.
*Color of the lobes of the compound tepal.*—Yellow.
*Development of the lobes of the compound tepal.*—Very developed.
*Color of the free tepal.*—Translucent white.
*Shape of the free tepal.*—Oval.
*Appearance of free tepal.*—More or less smooth.
*Apex of the free tepal.*—Medium developed.
*Shape of the apex of free tepal.*—Triangular.
*Length of anthers.*—Less than compound tepal.
*Color of filament.*—Cream.
*Color of anther (dorsal face).*—Cream.
*Color of the pollen sacs.*—Cream.
*Pollen.*—Medium.
*Basic color of style.*—White.
*Purple pigmentation of style.*—Absent.
*Length of style.*—Equal to compound tepal.
*Shape of style.*—Straight.
*Color of stigma.*—Pale yellow.
*Shape of ovary.*—Straight.
*Basic color of ovary.*—Cream.
*Pigmentation of the ovary.*—Without red/purple.
*Dominant color of male flower.*—Cream.
*Irregular flowers.*—Absent.
*Arrangement of ovules.*—Regular in two rows.

Characteristics of the fruit:

*Position of fruit.*—Curved upwards.
*Number of fruits in the middle hand.*—Medium 12–14.
*Length of fruit.*—Long.
*Shape of fruit.*—Straight in the distal part.
*Transverse section of fruit.*—Slightly ridged.
*Apex of fruit.*—Pointed.
*Remains of flower parts at apex of fruit.*—Base of the style prominent.
*Length of pedicel of fruit.*—Medium.
*Width of pedicel of fruit.*—Medium.
*Hairiness of pedicel.*—Not hairy.
*Fusion of pedicels.*—Not fused.
*Color of fruit skin before maturity.*—Light green (Plate 20-F-1).
*Color of skin after maturity.*—Yellow.
*Thickness of skin.*—Medium.
*Adherence of the skin.*—Fruit peels easily.
*Presence of cracks in skin.*—No.
*Presence of pulp.*—Yes.
*Color of the pulp before maturity.*—Ivory.
*Color of the pulp after maturity.*—Yellow.
*Fruit falling before maturity.*—No.
*Fruit is eaten.*—Cooked green and/or ripe.
*Texture of pulp.*—Firm.
*Taste.*—Mild.
*Main use.*—Cooking banana.
*Presence of seeds with source of pollen.*—Few.
*Appearance of seeds.*—Smooth.
*Shape of seeds.*—Flat.

Agronomic characteristics (averages taken during 1994–95 for first crop of 10 plants with no control of diseases); bunch data are from bunches which had been pruned to leave only the first 5 hands for development in accordance with this recommended practice:

*Days from planting to first flowering.*—306.
*Number of leaves at flowering.*—12.
*Number of functional leaves (less than 15% of area necrotic) at flowering.*—12.
*Number of leaves at harvest.*—8.
*Number of functional leaves (less than 15% of area necrotic) at harvest.*—5.
*Days from flowering until harvest.*—96.
*Bunch weight.*—19.5 kg.
*Number of hands.*—5.0.
*Finger length.*—23.8 cm.
*Finger diameter.*—4.0 cm.
*Number of fingers per bunch.*—69.0.
*Days from first flowering until second flowering.*—245.

Variance in botanical details: The plantain plant and its fruit described above may vary slightly in detail due to cultural practices, soil types and climatic conditions under which the variety may be grown; the present description is that of the variety grown under the ecological conditions prevailing on the FHIA experimental station near La Lima, Honduras.

I claim:

1. A new and distinct variety of plantain plant, substantially as illustrated and described, which has a high level of resistance to the black Sigatoka leaf spot disease; the fruit is further characterized by having a very good flavor when fried as green chips, an excellent flavor and texture when microwaved ripe, and to having size and shape characteristics closely resembling those of the reference False Horn variety when the bunches are pruned after emergence to leave only the first 5 hands for development.

* * * * *